United States Patent
Murata et al.

(10) Patent No.: US 6,407,282 B1
(45) Date of Patent: Jun. 18, 2002

(54) PROCESS FOR PRODUCING MONOESTER FROM DICARBOXYLIC ACID FLUORIDE

(75) Inventors: Hiroaki Murata; Sunao Ikeda; Satoru Saito, all of Kitaibaraki (JP)

(73) Assignee: Nippon Mektron, Limited (JP)

( * ) Notice: Subject to any disclaimer, the term of this patent is extended or adjusted under 35 U.S.C. 154(b) by 0 days.

(21) Appl. No.: 09/699,656

(22) Filed: Oct. 30, 2000

(30) Foreign Application Priority Data

Nov. 4, 1999 (JP) ............................................. 11-313204
Aug. 1, 2000 (JP) ........................................ 2000-232599

(51) Int. Cl.$^7$ ............................................... C07C 69/66
(52) U.S. Cl. ....................... 560/184; 560/180; 560/177; 562/401; 562/850
(58) Field of Search ................................. 560/177, 180, 560/184; 562/850, 401

(56) References Cited

U.S. PATENT DOCUMENTS 3,114,778 A    12/1963    Fritz et al.
4,131,740 A  * 12/1978    England ..................... 560/180
4,495,364 A  *  1/1985    Yamabe et al. ............. 560/180

FOREIGN PATENT DOCUMENTS

JP        53-3017         1/1978

* cited by examiner

*Primary Examiner*—Gary Geist
*Assistant Examiner*—Zachary Tucker
(74) *Attorney, Agent, or Firm*—Baker & Daniels

(57) ABSTRACT

Monoester monoacid fluoride of dicarboxylic acid is produced by allowing dicaroxylic acid fluoride represented by the following general formula:

$$FOCCF(CF_3)OCF_2(A)p(CF_2)qCOF$$

where A is a bifunctional perfluorinated group having 1 to 10 carbon atoms; p is 0 or 1; and q is 0 or an integer of 1–10, to react with an alcohol having at least 3 carbon atoms, thereby esterifying the terminal $CF_2COF$ group. Such selective monoesterification reaction is effective for separation and purification of a dicarboxylic acid difluoride isomer mixture comprising symmetrical dicarboxylic acid difluoride and asymmetrical dicarboxylic acid difluoride.

4 Claims, No Drawings

PROCESS FOR PRODUCING MONOESTER FROM DICARBOXYLIC ACID FLUORIDE

BACKGROUND OF THE INVENTION

1. Field of the Invention

The present invention relates to a process for producing a monoester from dicarboxylic acid fluoride, and more particularly to a process for producing monoester monoacid fluoride of dicarboxylic acid useful as a starting material for synthesis of perfluorovinyl ether from dicarboxylic acid fluoride.

2. Related Art

Perfluorovinyl ether is a useful monomer for use in fluorine-containing elastomers, etc. and its synthesis is carried out by converting the acid fluoride group of monoester monoacid fluoride of dicarboxylic acid to a carboxylic acid salt, followed by thermal decomposition reaction (JP-B-53-33572 and 53-33573).

$$FOCCF(CF_3)O(CF_2CFXO)p(CF_2)qCOOR$$

$$\downarrow$$

$$MOOCCF(CF_3)O(CF_2CFXO)p(CF_2)qCOOR$$

$$\downarrow$$

$$CF_2{=}CFO(CF_2CFXO)p(CF_2)qCOOR$$

$$\downarrow$$

Monoester monoacid fluoride of dicarboxylic acid for this purpose can be obtained usually by allowing dicarboxylic acid fluoride to react with an equimolar amount of alcohol, thereby esterifiying the acid fluoride group on one side. In that case, selectivity will be increased in a lower molar ratio of alcohol as a reactant, but a larger amount of unreacted dicarboxylic acid fluoride will remain, resulting in poor conversion. On the other hand, the conversion will be increased in a higher molar ratio of alcohol as a reactant, but the yield of diester will be increased, resulting in poor selectivity.

SUMMARY OF THE INVENTION

An object of the present invention is to provide a process for producing monoester monoacid fluoride of dicarboxylic acid from dicarboxylic acid fluoride with higher conversion and selectivity, resulting in higher yield.

The object of the present invention can be attained according to a process for producing monoester monoacid fluoride of dicarboxylic acid, which comprises allowing a dicarboxylic acid fluoride represented by the following general formula:

$$FOCCF(CF_3)OCF_2(A)p(CF)qCOF$$

where A is a bifunctional perfluorinated group having 1 to 10 carbon atoms; p is 0 or 1; and q is an integer of 1 to 10, to react with an alcohol having at least 3 carbon atoms, thereby esterifying the terminal $CF_2COF$ group.

DETAILED DESCRIPTION OF THE INVENTION

JP-B-57-61339 discloses that asymmetrical dicarboxylic acid fluoride represented by the foregoing general formula can be obtained by allowing dicarboxylic acid fluoride represented by the following general formula:

$$FOC(A)p(CF_2)qCOF$$

to react with hexafluoropropylene oxide (U.S. Pat. No. 3,114,778) or by allowing perfluorolactone to react with hexafluoropropene oxide (JP-A-53-3017), where A is a branched or unbrached bifunctional perfluorinated group capable of containing one or more ether bonds, represented e.g. by the following general formula:

$$[CF(CF_3)OCF_2]m(Rf)n{-}$$

Rf: Straight or branched perfluoroalkylene group having 1 to 10, preferably 1 to 4 carbon atoms
m: 0, 1 or 2
n: 0 or 1

Dicarboxylic acid fluoride includes, for example, the following compound:

$FOCCF(CF_3)OCF_2COF$
$FOCCF(CF_3)O(CF_2)_2COF$
$FOCCF(CF_3)O(CF_2)_3COF$
$FOCCF(CF_3)O(CF_2)_4COF$
$FOCCF(CF_3)O(CF_2)_5COF$
$FOCCF(CF_3)OCF_2CF(CF_3)OCF_2COF$
$FOCCF(CF_3)OCF_2CF(CF_3)O(CF_2)_2COF$
$FOCCF(CF_3)OCF_2CF(CF_3)O(CF_2)_3COF$
$FOCCF(CF_3)OCF_2CF(CF_3)O(CF_2)_4COF$
$FOCCF(CF_3)OCF_2CF(CF_3)O(CF_2)_5COF$

Alcohols for use in the reaction with these dicarboxylic acid fluorides include, for example, alcohols having at least 3 carbon atoms, such as propanol, isopropanol, n-butanol, isobutanol (2-butanol), 2-methyl-1-propanol, 4-heptanol, 2,2-dimethyl-1-propanol, 2,4-dimethyl-3-pentanol, etc. Above all, alcohols with a branched group are preferable.

Reaction is carried out between one part by mole of dicarboxylic acid fluoride and 0.7-2 parts by mole, preferably about 1- about 1.5 parts by mole, of an alcohol at a reaction temperature of about −60° to about 60° C. Selectivity can be increased at a lower reaction temperature, but from the viewpoint of cooler capacity, economy, etc. a reaction temperature of about −40° to about 20° C. is preferable. Reaction can be carried out in the presence of a solvent. A any solvent can be used, so long as it will not inhibit the reaction. Diglyme, tetraglyme, etc. used in the synthesis of dicarboxylic acid fluoride are preferable as solvents. Hydrogen fluoride, which is a by product of condensation reaction, is adsorbed onto an alkali metal fluoride such as sodium fluoride, etc. added to the reaction system as an acid-removing agent, and thus corrosion, etc. of reactors can be prevented.

Copolymers obtained by copolymerization with perfluorovinyl ether can be effectively used as functional, fluorine-containing polymers in the field of water- and oil-repellents, etc. Monoester monoacid fluoride of dicarboxylic acid having a perfluoroether bond, $FOCCF(CF_3)OCF_2(A)p(CF_2)qCOOR$, which is an intermediate for the synthesis of perfluorovinyl ether as a component for such copolymers, can be produced with good conversion and selectivity by using an alcohol having at least 3 carbon atoms as an esterifying agent.

Selective monoesterification reaction of such a asymmetrical dicarboxylic acid difluoride can be effectively used for separation and purification of a mixture of dicarboxylic acid difluoride isomers which comprises symmetrical dicarboxylic acid difluoride and asymmetrical dicarboxylic acid difluoride.

By allowing dicarboxylic acid difluoride represented by the following general formula [A]:

$$FOCCF(CF_3)O(CF_2)_{n+2}OCF(CF_3)COF \quad [A]$$

to react with an alkali metal carbonate such as sodium carbonate, potassium carbonate, etc., a perfluorodivinyl ether represented by the following formula can be synthesized:

$$CF_2=CFO(CF_2)_{n+2}OCF=CF_2$$

Dicarboxylic acid difluoride [A] can be synthesized by allowing dicarboxylic acid difluoride represented by the following general formula:

$$FOC(CF_2)_nCOF$$

to react with hexafluoropropene oxide (U.S. Pat. No. 3,114, 778), but dicarboxylic acid difluoride represented by the following general formula [B] is inevitably by-product at the same time:

$$FOCCF(CF_3)OCF_2CF(CF_3)O(CF_2)_{n+1}COF \quad [B]$$

These dicarboxylic acid difluorides [A] and [B] are isomers with the same molecular weight and with no substantial difference in boiling point, and thus are very difficult to separate from each other by ordinary distillation procedures.

The foregoing selective monoesterification reaction of the present invention can be effectively used for efficient separation and purification of only desired dicarboxylic acid difluoride from a mixture of dicarboxylic acid difluoride isomers with the same molecular weight and with no substantial difference in boiling point.

That is, a mixture of dicarboxylic acid difluoride isomers, which comprises an isomer represented by the following general formula [A]:

$$FOCCF(CF_3)O(CF_2)_{n+2}OCF(CF_3)COF \quad [A]$$

where n is 0 or an integer of 1 or more, and an isomer represented by the following general formula [B]:

$$FOCCF(CF_3)OCF_2CF(CF_3)O(CF_2)_{n+1}COF \quad [B]$$

where n is 0 or an integer of 1 or more, is allowed to react with a branched alcohol having at least 3 carbon atoms, thereby monoesterifying the terminal $CF_2COF$ group of isomer [B], and then isomer [A] is separated and purified therefrom by distillation and obtained as desired dicarboxylic acid difluoride.

Alcohols for use in the monoesterification of terminal carboxylic acid fluoride group of the isomer mixture comprising dicarboxylic acid difluorides [A] and [B] include, for example, branched alcohols having at least 3 carbon atoms such as 2-propanol, 2-methyl-1-propanol, 4-heptanol, 2,2-dimethyl-1-propanol, 2,4-dimethyl-3-pentanol, etc.

In the monoesterification reaction with a branched alcohol of such a stereoselectivity, monoesterification reaction of asymmetrical dicarboxylic acid difluoride [B] takes place preferentially, thereby facilitating separation of dicarboxylic acid difluoride [A] from [B] by distillation procedures. In the case of using an alcohol having one or two carbon atoms or an unbranched alcohol having even at least 3 carbon atoms, monoesterification reaction of dicarboxylic acid fluorides [A] and [B] takes place substantially in parallel, resulting in decreased recovery rate of dicarboxylic acid difluoride [A].

Monoesterification reaction of asymmetrical dicarboxylic acid difluoride [B] can be carried out at a reaction temperature of about −60° to about 60° C. with 0.5–10 parts by mole, preferably about 1 to about 4 parts by mole, of an alcohol per part by mole of isomer [B]. Selectivity can be increased at a lower reaction temperature, but from the viewpoint of cooler capacity, economy, etc., a reaction temperature of about −40° to about 20° C. is preferable. Reaction can be carried out in the presence or the absence of a solvent. Any solvent can be used, so long as it will not inhibit the reaction. Diglyme, tetraglyme, etc. used in the synthesis of dicarboxylic acid difluoride are preferable as solvents. Hydrogen fluoride, which is a by product of condensation reaction, is adsorbed onto an alkali metal fluoride such as sodium fluoride, etc. added to the reaction system as an acid-removing agent, and thus corrosion, etc. of reactors can be prevented.

A mixture of monoesterified dicarboxylic acid difluoride isomers is a mixture comprising dicarboxylic acid difluorides [A] and [B], and their monoesterified compounds. Complete monoesterification of dicarboxylic acid difluoride [B] can be attained by using much more alcohol than isomer [B], but elimination of dicarboxylic acid difluoride [B] by the complete monoesterification of [B] will lower the recovery rate of dicarboxylic acid difluoride [A]. Thus, it is necessary to restrict the monoesterification of dicarboxylic acid difluoride [B] to about 80%, thereby maintaining an appropriate recovery rate of dicarboxylic acid difluoride [A].

In the mixture of monoesterified dicarboxylic acid disulfide isomers comprising the foregoing components, a considerable proportion of dicarboxylic acid difluoride [B] is monoesterified, and thus dicarboxylic acid difluoride [A] can be separated and purified with a high purity from the mixture by distilling the mixture under atmospheric or subatmospheric conditions.

In other words, dicarboxylic acid difluoride can be obtained as a mixture of isomers with no substantial difference in boiling point by reaction of $FOC(CF_2)_nCOF$ with hexafluoropropene oxide, and a dicarboxylic acid difluoride isomer useful for an intermediate to synthesis of perfluorodivinyl ether can be obtained easily with a high purity by monoesterification of the isomer mixture with a specific branched alcohol, followed by distillation of the monoesterified isomer mixture.

PREFERRED EMBODIMENTS OF THE INVENTION

The present invention will be described in detail below, referring to Examples and Comparative Examples.

REFERENCE EXAMPLE 1

327 g (1.1 mole) of perfluoroadipic acid fluoride was subjected to reaction with 199.2 g (1.2 moles) of hexafluoropropene oxide at 0°–5° C. in the presence of 15.2 g (0.1 mole) of cesium fluoride and 300 ml of diglyme, and the reaction mixture was distilled to obtain dicarboxylic acid fluoride $FOCCF(CF_3)O(CF_2)_6COF$.

EXAMPLE 1

300 g (0.65 moles) of $FOCCF(CF_3)O(CF_2)_5COF$ obtained in Reference Example 1 and 33 g of sodium fluoride were charged into a 500-ml glass reactor vessel and stirred, while keeping the inside temperature at −30° to −20° C., and 42.9 g (0.72 moles) of propanol was dropwise added thereto over 2 hours. After the dropwise addition, sodium fluoride was filtered off, whereby 287 g of a reaction mixture comprising 15.8% by mole of the starting material, 48.5% by mole of monoester and 35.7% by mole of diester was obtained with conversion of 84.2%, monoester selectivity of 57.6% and yield of 42.8%.

EXAMPLE 2

In Example 1, the same amount of isopropanol was used in place of propanol, whereby 285 g of a reaction mixture comprising 11.4% by mole of the starting material, 59.1% by mole of monoester and 25.6% by mole of diester was obtained with conversion of 88.6%, monoester selectivity of 69.8% and yield of 51.8%.

EXAMPLE 3

In Example 1, 63.3g (0.72 moles) of 2,2-dimethyl-1-propanol dissolved in 30 g of tetraglyme was used in place of propanol, whereby 328 g of a reaction mixture comprising 6.8% by mole of the starting material, 74.0% by mole of monoester and 17.0% by mole of diester was obtained with conversion of 93.2%, monoester selectivity of 81.3% and yield of 70.4%.

EXAMPLE 4

In Example 1, 234 g (0.65 moles) of $FOCCF(CF_3)O(CF_2)_3COF$ was used as dicarboxylic acid fluoride and 83.5 g (0.72 moles) of 2,4-dimethyl-3-pentanol was used in place of propanol, whereby 256 g of a reaction mixture comprising 5.8% by mole of the starting material, 78.4% by mole of monoester and 15.8% by mole of diester was obtained with conversion of 94.2%, monoester selectivity of 83.2% and yield of 67.7%.

EXAMPLE 5

In Example 1, 202 g (0.65 moles) of $FOCCF(CF_3)O(CF_2)_2COF$ was used as dicarboxylic acid fluoride and 83.5 g (0.72 moles) of 2,4-dimethyl-3-pentanol was used in place of propanol, whereby 220 g of a reaction mixture comprising 6.7% by mole of the starting material, 76.6% by mole of monoester and 16.7% by mole of diester was obtained with conversion of 93.3%, monoester selectivity of 82.1% and yield of 63.9%.

COMPARATIVE EXAMPLE 1

In Example 1, 22.9 g (0.72 moles) of methanol was used in place of propanol, whereby 262 g of a reaction mixture comprising 19.0% by mole of the starting material, 42.9% by mole of monoester and 38.1% by mole of diester was obtained with conversion of 81.0%, monoester selectivity of 53.0% and yield of 36.6%.

REFERENCE EXAMPLE 2

151 g of diglyme as a reaction solvent and 11.7 g of cesium fluoride as a catalyst were charged into a 500-ml glass reactor vessel with a dry ice-methanol condenser and stirred while cooling to make the inside temperature 0° C. After pressure reduction, 50 g (0.26 moles) of $FOC(CF_2)_2COF$ was charged thereto, and 300 g (0.65 moles) of hexafluoropropene oxide was dropwise added thereto over 3 hours.

After the dropwise addition, the reaction mixture was allowed to stand to make phase separation, and 409.5 g of a dicarboxylic acid difluoride isomer mixture comprising the following compounds (A) and (B) was obtained as a lower phase separated from the upper diglyme phase:

| | |
|---|---|
| (A) $FOCCF(CF_3)O(CF_2)_4OCF(CF_3)COF$ | 71.5% by mole |
| (B) $FOCCF(CF_3)OCF_2CF(CF_3)O(CF_2)_3COF$ | 28.5% by mole |

EXAMPLE 6

21.0 g (0.04 moles) of the dicarboxylic acid difluoride isomer mixture obtained in Reference Example 2 and 2 g of NaF as an acid-removing agent were charged into a 100-ml glass reactor vessel, and 2.7 g (2.05 parts by mole per part by mole of component (B) in the isomer mixture) of 4-heptanol was added thereto, while cooling the reactor vessel with ice water.

21.3 g of esterification reaction mixture was obtained and analysis of the reaction mixture by gas chromatography revealed that 27.2% by mole of the initial 71.5% by mole of component (A) was changed to monoester, while 44.3% by mole thereof was not changed, whereas all of the initial 28.5% by mole of component (B) was monoesterified.

The esterification reaction mixture was distilled under subatmospheric pressure in a distillation apparatus with a vigoureux tube, 10 mm in diameter and 100 mm long, and 6.3 g of a distillate at a distillation temperature of 50°–60° C. (30 Torr) was recovered. The distillate was found to be component (A) of 99.0% purity by gas chromatography.

EXAMPLE 7

In Example 6, esterification reaction was carried out with 2.0 g (1.50 part by mole per part by mole of component (B) in the isomer mixture) of 2,4-dimethyl-3-pentanol in place of 4-heptanol, whereby 21.2 g of esterification reaction mixture was obtained, where 13.9% by mole of the initial 71.5% by mole of component (A) was changed to monoester, while 57.6% by mole thereof was not changed, whereas 27.6% by mole of the initial 28.5% by mole of component (B) was changed to monoester, while 0.9% by mole thereof was not changed.

The esterification reaction mixture was distilled in subatmospheric pressure in the same manner as in Example 6, where component (A) of 98.9% purity was recovered.

EXAMPLE 8

In Example 6, 23.8 g (0.05 moles) of dicarboxylic acid difluoride isomer mixture comprising 90.9% by mole of component (A) and 9.1% by mole of component (B) was subjected to esterification reaction with 2.0 g (3.8 parts by mole per part by mole of component (B) in the isomer mixture) of 2,4-dimethyl-3-pentanol in place of 4-heptanol in the presence of 0.5 g of NaF, whereby 21.2 g of the esterification reaction product was obtained, where 19.2% by mole of the initial 90.9% by mole of component (A) was changed to monoester, while 71.7% by mole thereof was not changed, whereas 8.3% by mole of the initial 9.1% by mole of component (B) was changed to monoester, while 0.8% by mole thereof was not changed.

The esterification reaction mixture was distilled in a distillation apparatus with a vigoureux tube, 10 mm in diameter and 100 mm long, and 11.8 g of a distillate at a distillation temperature of 110°–112° C. was recovered. The distillate was found to be component (A) of 98.9% purity.

COMPARATIVE EXAMPLE 2

In Example 6, esterification reaction was carried out with 0.55 g (1.50 part by mole per part by mole of component (3)

in the isomer mixture) of methanol in place of 4-heptanol, whereby 20.3 g of the esterification reaction mixture was obtained, where 29.6% by mole of the initial 71.5% by mole of component (A) was changed to monoester, while 41.9% by mole thereof was not changed, whereas 13.4% by mole of the initial 28.5% by mole of component (B) was changed to monoester, while 15.1% by mole thereof was not changed.

What is claimed is:

1. A process for producing monoester monoacid fluoride of dicarboxylic acid, which comprises allowing asymmetrical dicarboxylic acid fluoride represented by the following general formula:

$$FOCCF(CF_3)OCF_2(A)_p(CF_2)_qCOF$$

, where A is a bifunctional perfluorinated group having 1 to 10 carbon atoms; p is 0 or 1; and q is 0 or an integer of 1–10, to react with 2,2-dimethyl-1-propanol or 2,4-dimethyl-3-pentanol, thereby esterifying the terminal $CF_2COF$ group.

2. A process according to claim 1, wherein the group A in the general formula for the asymmetrical dicarboxylic acid fluoride is a divalent group represented by the following general formula:

$$-[CF(CF_3)OCF_2]_m(Rf)_n-$$

, where Rf is a perfluoroalkylene group having 1 to 10 carbon atoms; m is 0, 1 or 2; and n is 0 or 1.

3. A process for separating and purifying dicarboxylic acid difluoride, which comprises:

providing a mixture of dicarboxylic acid difluoride isomers represented by the following general formulae:

$$FOCCF(CF_3)O(CF_2)_{n+2}OCF(CF_3)COF \quad [A]$$

, where n is 0 or an integer of 1 or more, and $$FOCCF(CF_3)OCF_2CF(CF_3)O(CF_2)_{n+1}COF \quad [B]$$

, where n is 0 or an integer of 1 or more, said isomer mixture being obtained by reacting dicarboxylic acid difluoride represented by the following general formula:

$$FOC(CF_2)_nCOF$$

, where n is 0 or an integer of 1 or more with hexafluoropropene oxide, reacting said mixture with 4-heptanol or 2,4-dimethyl-3-pentanol, thereby monoesterifying the terminal $CF_2COF$ group of component [B], and then distilling the reaction mixture, thereby recovering component [A] as a distillate.

4. A process according to claim 3, where 0.5–10 parts by mole of the alcohol is used per part by mole of component [B].

* * * * *